Figure 4:
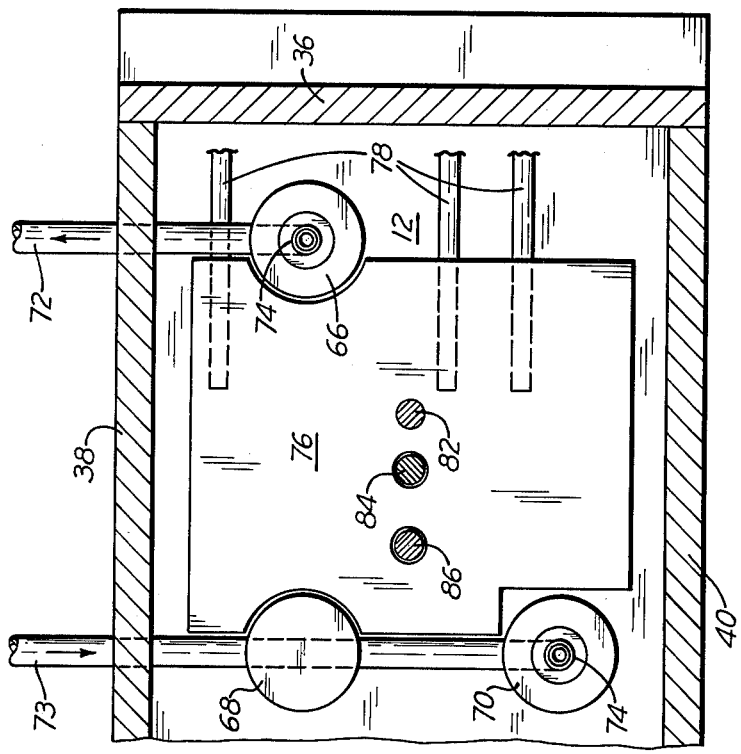

United States Patent [19]

Wolfe

[11] 4,082,459
[45] Apr. 4, 1978

[54] ANALYTICAL CELL ASSEMBLY FOR AN ANALYZER

[75] Inventor: Court Lone Wolfe, Pittsburgh, Pa.

[73] Assignee: Chemed Corporation, Cincinnati, Ohio

[21] Appl. No.: 690,627

[22] Filed: May 27, 1976

[51] Int. Cl.² .................................. G01N 21/52
[52] U.S. Cl. .................... 356/85; 250/458; 250/576; 356/246
[58] Field of Search ............ 356/51, 85, 244, 246, 356/181; 250/343, 373, 461, 458, 573, 574, 576

[56] References Cited

U.S. PATENT DOCUMENTS

| 2,999,417 | 9/1961 | Isreeli | 356/246 |
| 3,711,708 | 1/1973 | Dolin et al. | 356/246 X |
| 3,861,809 | 1/1975 | Hall, Jr. | 356/246 |
| 3,906,226 | 9/1975 | Okabe et al. | 250/373 X |

*Primary Examiner*—F. L. Evans
*Attorney, Agent, or Firm*—William Kovensky; William W. McDowell, Jr.

[57] ABSTRACT

An analytical cell assembly comprising a base with a radiation source mounted on one end, an enclosure on the other end, and a cell proper, with cell heating means, within the enclosure. The enclosure and cell have cooperative fluid flow connections whereby the cell is modular and may be simply lifted out of the enclosure. The enclosure also includes a collimating lens assembly interposed between the cell within the enclosure and the source outside the enclosure on the base. The entire assemblage of source, enclosure and cell can be moved as a unit, making it modular, or just the cell can be moved as a module leaving the enclosure and the source in place in an instrument using the invention cell assembly.

16 Claims, 5 Drawing Figures

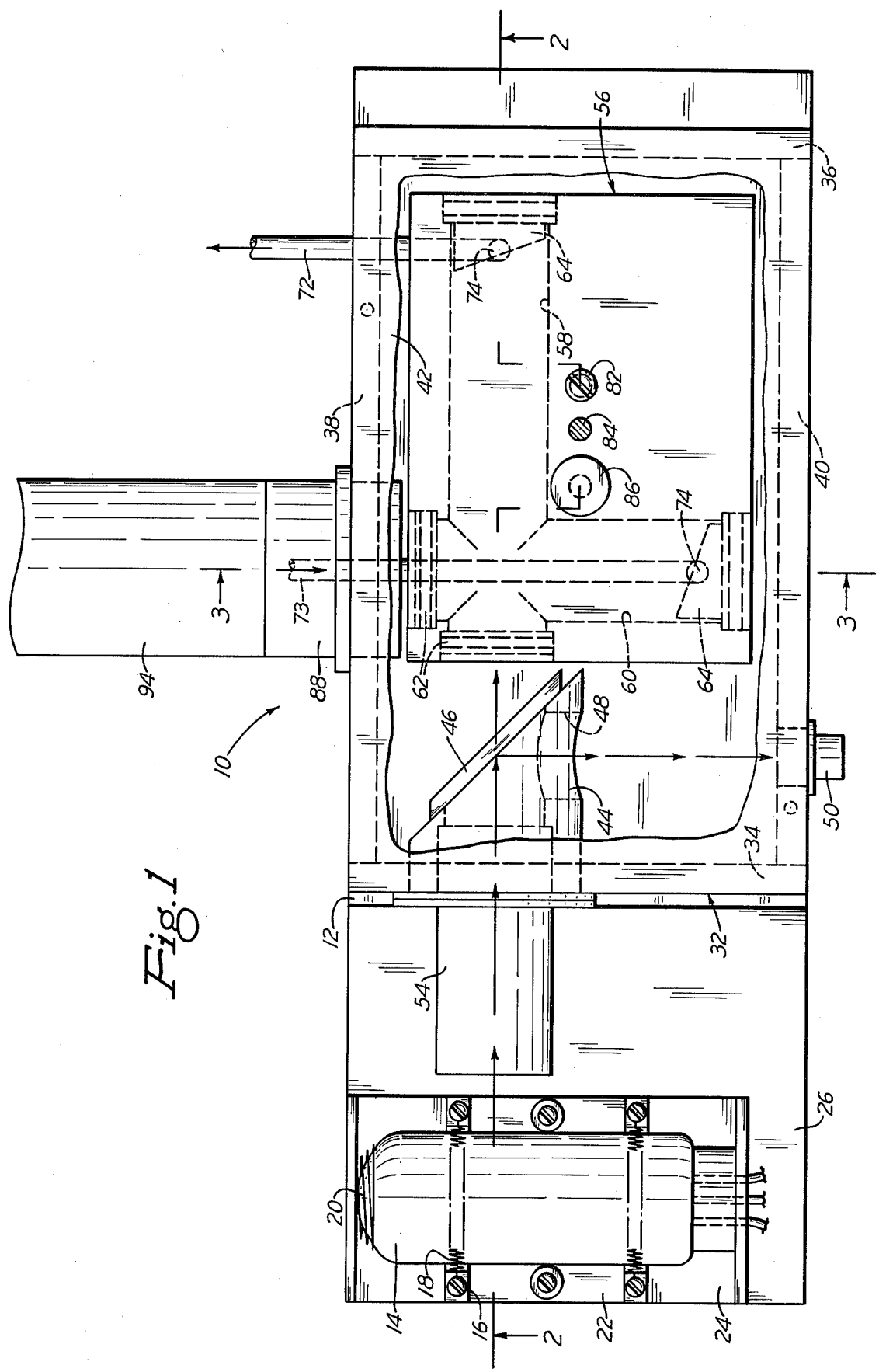

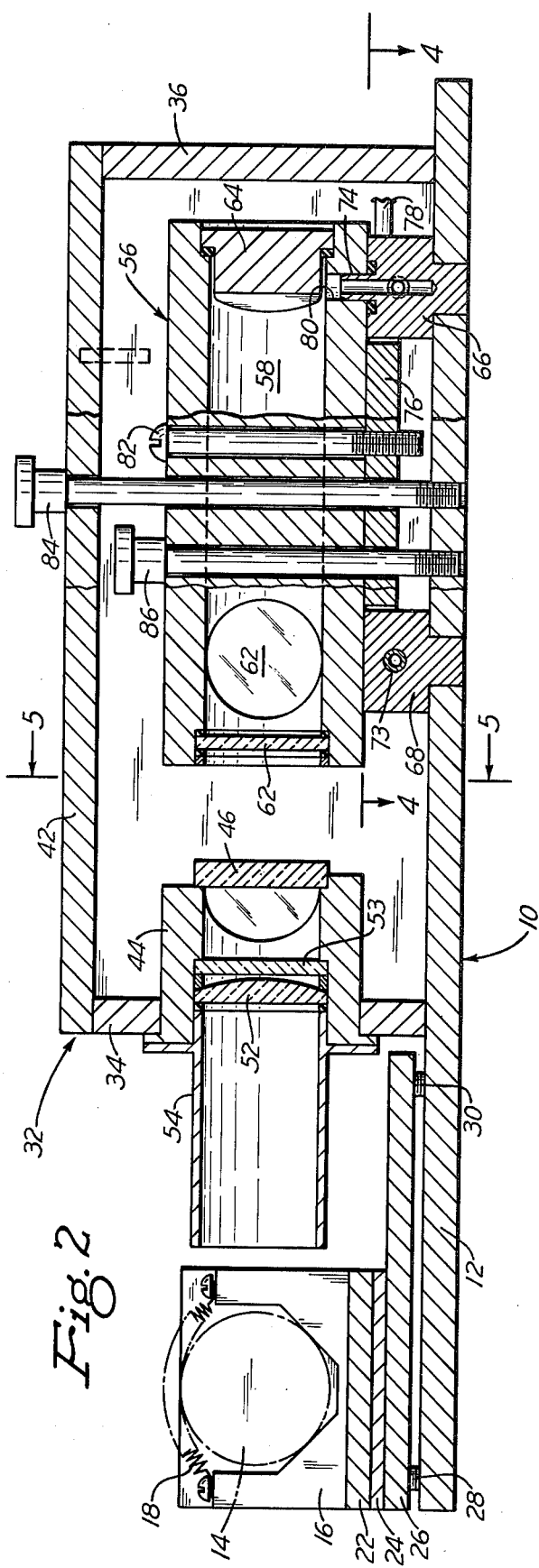

ANALYTICAL CELL ASSEMBLY FOR AN ANALYZER

The present invention is an improved analytical cell assembly, particularly suitable for use in flow type fluorescent gas analyzers.

It has long been known that certain materials will re-emit light, will fluoresce, when exposed to certain radiation sources. In recent times, this phenomenon has been utilized in analytical devices, particularly for gaseous streams, and still more particularly for detecting pollutants in air.

The present invention pertains to a subassembly of such analyzers, more particularly to an improved cell, housing for the cell, and overall modular unit including the cell, housing, a radiation source, and a base member for carrying all the above parts, to permit rapid assembly and disassembly of the above into such analyzers as needed.

The analytical portions of analyzers have for many years presented numerous problems which are overcome by the present invention. Firstly, many such prior sample cells have been permanently mounted. The present invention provides a cell which is readily removable from the device with which it is used, i.e., the cell per se is a separate module. This removability permits easy cleaning, maintenance, replacement of parts, and the like of the cell, which services were heretofore extremely difficult to perform, often requiring substantial amounts of disassembly of the analyzer.

The removable modular cell includes many features which were heretofore present in and around the cell. Certain filters, light traps, lenses, parts of the optical system, flow connections for the sample, and the like, are all built integrally into the cell. The invention also includes a heater mounted in heat conducting contact with the cell to facilitate keeping the sample being irradiated at a known predetermined temperature.

The sample cell is mounted in a cabinet or enclosure which includes flow fittings which cooperate with orifices in the cell to connect or disconnect the flow paths to other parts of the analytical device automatically when the cell is moved into or out of position in the enclosure. An arrangement of screws to hold the heating means on the cell, to hold the cell in the enclosure, and to locate and hold the lid on the cabinet in proper position with respect to the cell therein, is provided.

Another aspect is the base member of this enclosure, one end of which is extended and mounts the radiation source thereon. These mounting means have the ability of moving the source in all three degrees of freedom, and to thereafter secure the source in place with respect to the base extension, so that the source, the optics and the cell are in a permanent prefocused factory calibrated arrangement with respect to each other. In this manner, no field adjustment is required, and accuracy of results is improved, while its use is greatly simplified. The enclosure includes a portion of the optics which are positioned and adjusted between the cell inside the enclosure, and the source without the enclosure to achieve this prefocused arrangement.

The invention provides therefore a dual modular arrangement; the cell proper is mounted in a modular manner within the enclosure. The enclosure, with the cell therein and the source mounted on the extended base member, is also modular with respect to the analytical instrument with which the invention is used. In other environments, the enclosure can be made large enough to enclose both the cell and the radiation source, which may be desirable depending upon any particular set of requirements.

The invention is constructed of readily available parts, without the use of any complicated subassemblies or components, to thereby permit its fabrication in a relatively facile manner, and to produce a relatively inexpensive device, which at the same time is highly efficient in use to achieve its advantages and results. The invention is also made of readily available parts and materials, requiring no special skills or manufacturing methods for its fabrication.

Figure 5:
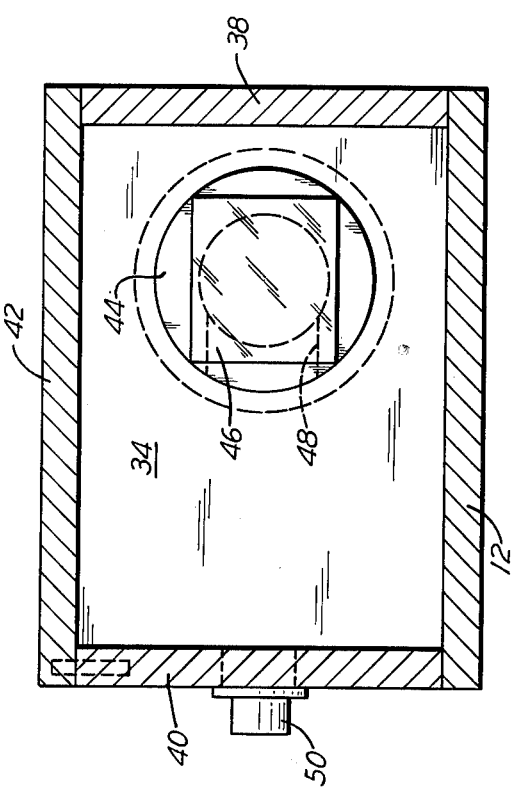

The above and other advantages of the invention will be pointed out or will become evident in the following detailed description and claims, and in the accompanying drawing also forming a part of the disclosure, in which:

FIG. 1 is a plan view of a preferred form of the invention, with some parts broken away and in cross-section for the sake of clarity; FIGS. 2 and 3 are vertical cross-sectional views taken on lines 2—2 and 3—3 respectively of FIG. 1; FIG. 4 is a partial plan view taken on line 4—4 of FIG. 2; and FIG. 5 is a vertical cross-sectional view taken on line 5—5 of FIG. 2.

Referring now in detail to the drawing, reference numeral 10 indicates a preferred embodiment of the present invention. The assembly 10 is built upon a base plate 12, which may comprise simply a rectangular flat piece of metal simply machined to mount the other parts thereon.

At its left end, base 12 mounts a radiation source, shown in the form of bulb 14, which is held in a cradle member or assembly 16 by means of hold-down means 18 which may conveniently comprise springs stretched slightly across the top of the bulb or light source and held in place by suitable screws and the like. Depending upon the particular gas being analyzed, the source 14 can be any of several different types. For example, a dueterium lamp, a Zenon lamp of various types, a Zinc, Lead or Antimony source, an RF source, a hydrogen lamp, or any other source emitting electromagnetic radiation of the appropriate wavelength could be used. Shock mounting means in the form of a relatively "soft" large diameter spring 20, can be provided at the end of the source 14 to protect against shocks.

Means are provided to move the source 14 with respect to base 12 and with respect to the other parts of the invention described below. To this end, a pair of members 22 and 24 are provided, see FIG. 2, for the purpose of adjusting source 14 in planes parallel to base 12. Further, means are provided to adjust the vertical height of source 14 on base 12. To this end, another base member 26 is mounted on main base 12 by a pair of spring loaded adjustable mounts 28 and 30. The left end mount 28 includes spring means to normally urge the source upwardly with respect to base 12, and the mount 30 at the right end acts like a pivot or a hinge, and includes spring means to load that end of the base 26 downwardly. Mounts 28 and 30 are conventional, and therefore not described or shown in greater detail herein.

To the right of the source assembly, base 12 mounts an enclosure 32 comprising a pair of end walls 34 and 36 interconnected by a pair of side walls 38 and 40, and a lid 42.

The drawings show the preferred embodiment, i.e., the source mounted outside the cell. This arrangement provides the advantage that no additional cooling is required since the heat generated by the source is readily dissipated into the ambient atmosphere. However, there are certain minor concurrent disadvantages to this preferred arrangement; namely, an additional light shield is required to protect the eyes of persons who might be near the equipment, and the possibility that a careless person could touch a hot source bulb. Thus, it is within the teaching of the invention to make the enclosure, the walls 34 through 40 and the lid 42, large enough to enclose both the source and the cell. This would overcome the above disadvantages, but would generate a need for a fan or other ventilating means to dissipate the heat produced by the source to prevent that heat from adversely affecting the analytical results produced.

In the event both the source and the cell were within an enclosure, the means to direct the energy from the source to the cell, described immediately below, would be mounted, most likely, directly on the base 12, rather than on the enclosure end wall 34. All of such changes are mechanical and easily within the expertise of those skilled in these arts.

Enclosure end wall 34 carries means to direct the energy from source 14 and to pass it into the inside of the enclosure 32 and the parts therein. A beam collimator, interference filter, and beam splitter assembly is provided for this purpose and it comprises a housing member 44 which is positioned in a suitably formed opening in end wall 34 and mounts a light shield member 54 at its front end. The shape of the housing 44 can be best seen by simultaneously looking at FIGS. 1 and 2. The end of the housing 44 inside the closure 34 is cut at about a 45° angle, and it mounts a beam splitter member 46 at its front end. In the successfully constructed embodiment of the invention which was designed for use with a sulfur dioxide analyzer, beam splitter 46 was fabricated from a thin flat disk of high purity quartz which will transmit 98% of the UV energy of interest, and when arranged at a 40° angle to the incident beam will reflect approximately 4% of the radient energy onto the reference detector 50. An opening 48 is formed at right angles to the incident beam so that the reflected reference energy is free to pass out of the supporting means to the reference detector.

Rearwardly, to the left in the drawings, of the beam splitter 46, the housing 44 mounts a collimating lens 52 and an interference filter 53 all held in place by suitable O-rings, clamps, screws, and the like, most of which are not shown for the sake of clarity, in the usual manner for fabricating optical devices.

In the instrument for which the embodiment of the invention shown was built, the electronics portion operated upon a sample of the total energy passed through the housing 44, the predetermined portion of which was a function of the characteristics of the device 46. This sample energy was reflected off device 46 to a reference detector 50 mounted in the side wall 40. The wires and the like leading from this device in said successfully constructed embodiment are omitted in the drawings for the sake of clarity.

Within the enclosure 34 the invention comprises an analytical cell 56. Cell 56 is basically a rectilinear block of metal with a pair of openings 58 and 60 drilled therethrough at right angles to each other, as is best shown in FIG. 1. Two of the four ends of the two through openings are closed off by quartz window means and the other two by light trap means, as will be set forth in detail below. The intersection of these two through openings 58 and 60 is located to one corner of the cell, as appears clearly in FIG. 1.

The left hand end of the through opening 58, which faces the beam splitter 46, is provided with a quartz window 62, and other suitable means, including O-rings, retaining rings, mounting screws, a source stop, etc., all which are indicated generally and not described herein, and which are conventional in this art. The material of the window 62 however should be selected in conjunction with the wave length of the energy which is desired for purposes of irradiating the sample which will flow through the inside of the cell 56 through the passageways 58 and 60. The left hand end, see FIG. 3, of the other passageway 60, comprises an identical quartz window 62 and associated parts, however, a source stop is not required at this end of passageway 60. The opposite ends of both passageways 58 and 60 are provided with suitable light trap means 64, such as modified Wood light traps, for the purposes of preventing stray light which passes beyond the area of the fluorescent cloud of irradiated sample to reflect back into the photodetector which would have a detrimental effect on results. Further, as is known, it is advantageous to coat all internal surfaces of the cell, i.e. the traps 64 and the sides of the passageways 58 and 60, with a black Teflon coating which avoids water collection inside the cell, the black color also serving to dampen stray light.

Means are provided to locate and mount cell 56 in enclosure 32, and also to flow a stream of sample material to, through and out of the passageways 58 and 60 in the cell. To this end, referring to FIG. 4, the base plate 12 carries three mounting and locating pads 66, 68, and 70. A pair of lines 72 and 73 pass through suitably formed and sealed openings in the side wall 38. The supply line 72 passes through a clearance opening in the pad 68, and terminates at the pad 70. The passageway provided in the supply line 73 passes upwardly through pad 70, and terminates in a nozzle portion 74, which is also provided with a suitable seal in the form of an O-ring or the like. In a similar manner, the return line 72 begins from a similar nozzle portion 74 on the pad 66, and thence returns to other locations which are dictated by the particular installation with which the invention is being used. The pads 66, 68 and 70 are similar and each comprises an enlarged central body portion, the bottom shoulder of which rests against the base plate 12, and the upper shoulder of which cooperates with the bottom of the analytical cell 56 to form a seal therewith together with the O-ring or the like in nozzle portion 74. The third pad 68 serves as a support; it does not have a nozzle portion. The enlarged body portions of the three pads are used with the heater, as will be set forth below. Referring to FIG. 4, the heating means comprise a heater block 76 which is formed with a plurality of blind openings in which are mounted conventional heating elements with suitable control means 78. The leads to control and power the elements 78 are not shown in the drawing for the sake of clarity.

Thus, referring especially to FIG. 1, it can be seen that the flow of sample is in through the line 73, up through the nozzle 74 at the end of that line in the pad 70, through 60, through the intersection of the passageways 60 and 58 where the cloud of irradiated sample exists, and then through 58 and out through the line 72 via its nozzle portions 74. Vacuum or pump means, not shown, will be included in an analyzer with which the invention is used to drive this flow. The cell is formed with a pair of openings 80 each adapted to snugly receive a nozzle portion.

Means are provided to hold the heater block 76 up against the underside of the cell 56, to hold the cell 56 with the heater thereon in place on the pads 66, 68 and 70, and to hold the lid 42 down on the enclosure 32. To this end, three screws, 82, 84 and 86 are provided. Each screw has a different predetermined length to perform its particular function, see FIG. 1. The shortest screw 82 fits through a suitably formed clearance opening in the body of the cell 56, and terminates in a mating threaded opening in the body of the heater block 76. The body of the cell 56 is also formed with two other through clearance openings to receive the other two screws 84 and 86. Similarly, the heater block 76 is formed with a pair of through openings which mate with these through openings in the heater block to permit the screws 84 and 86 to pass therethrough. Screw 86 passes through these two registering clearance openings and cooperates with a mating threaded opening in the base 12 to hold cell 56, with or without the heater 76 secured to the underside thereof by its screw 82, down in the enclosure 32 against the three pads 66, 68 and 70. The screws 84 and 86 are provided with enlarged ends to facilitate their use with fingers only. The screw 84 is quite similar to the screw 86, it passes through a clearance opening in the lid 42, and then through two registering clearance openings in the cell 56 and in the heater block 76, finally cooperating with a threaded opening in the base 12. The head of screw 84 hold the lid down on the enclosure to complete the assembly.

As shown in FIG. 4, the heater block 76 is formed with cutouts to mate with and locate against the enlarged body portions of the pads 66 and 68, especially, and with a cutout corner to facilitate manufacture and to clear the third pad 70. In the preferred embodiment, this block 76 was made of aluminum because of its desirable heat transmission qualities. The heater with its control means provides the advantage of holding the cell 56 at any predetermined desired temperature, as dictated by the nature of the material being analyzed, to thereby enhance the results produced with the use of the invention. At its inner end, in closely spaced position to the window 62, the housing 88 carries another window 92 of the same material as the window 62.

The light guide 90 is a cylindrical section of a product trademarked "Hexacell". In cross section, it is in the form of a honeycomb (nested hexagonal sections) and has the effect of a multiplicity of small diameter, very thin wall parallel tubes nested together as a cylindrical unit. The light guide is blackened to reduce light reflection. It is used to limit the angle of view of the PM tube. At its inner end and closely positioned to the window 62 the housing 88 carries a color filter. The purpose of the color filter is to limit the spectral quality of the light reaching the photo detector to only that emitted by the fluorescent cloud.

At the outer end of the housing 88 there is provided a tubing member 94 in which some other instrumentation may be mounted to receive the energy from the cell 56. In the successfully constructed embodiment used with a sulfur dioxide analyzer, instrumentation within tube 94 was a photomultiplier tube.

While the invention has been described in detail above, it is to be understood that this detailed description is by way of example only, and the protection granted is to be limited only within the spirit of the invention and the scope of the following claims.

I claim:

1. In combination, a base member, source means mounted on said base member, a modular sample cell, means to removably mount said cell on said base member, an enclosure mounted on said base member enclosing at least said cell when it is mounted on said mounting means, means to flow sample to, through and thence out of said cell via said cell mounting means, means to direct the energy from said source means to said cell, said cell comprising a body member formed with intersecting fluid flow passageways extending through said body member, window means at an end of each passageway and light trap means at the opposite end of each passageway, heating means for said cell, and means to mount said heating means in contact with said cell.

2. The combination of claim 1, said cell body being of generally rectilinear configuration, said flow means comprising a flow inlet in one of said passageways and a flow outlet in the other of said passageways so positioned that sample will flow therebetween and through the intersection of said passageways, a plurality of mounting pads mounted on said base member to position said cell in predetermined spaced relation to said base member, said flow means further comprising an inlet and an outlet formed in respective ones of said pad members and cooperable with said cell flow inlet and outlet respectively, said heating means comprising a heater block configured to be positioned in said space between said cell and said base member when said cell is mounted on said pads and said flow means, and said heater block mounting means comprising a screw extending through said cell independently of said passageways therein and having its threaded end cooperating with a mating threaded opening in said heater block, whereby tightening of said screw at the head thereof on one side of said cell draws said heater block against the opposite side of said cell.

3. The combination of claim 2, and means to mount said cell with or without said heating means connected thereto in said enclosure comprising a screw extending through registering openings in said cell and said heater block when said heater block is mounted on said cell, and said screw comprising a threaded end fitting a threaded opening in said base member.

4. The combination of claim 2, and means to secure a lid on said enclosure and to locate said cell with or without said heating means connected thereto in said enclosure comprising a screw mounted in said lid and extending through registering openings in said block, independently of said passageways therein, and said heater block when mounted on said cell, and terminating at a mating threaded opening in said base member.

5. The combination of claim 1, means to mount an energy detection means in a wall of said enclosure in closely spaced relation to a window means in said cell, whereby the fluorescence re-emitted by the irradiated sample at the intersection of said passageways may be detected by means mounted on said energy detection mounting means.

6. In combination, a base member, source means mounted on said base member, a modular sample cell, means to removably mount said cell on said base member, an enclosure mounted on said base member enclosing at least said cell when it is mounted on said mounting means, means to flow sample to, through and thence out of said cell via said cell mounting means, means to direct the energy from said source means to said cell, heating means, means to mount said heating means in contact with said cell, whereby said cell and sample therein may be maintained at a predetermined temperature under the control of said heating means, said cell comprising a body member formed with intersecting fluid flow passageways extending through said body member, said flow means including an inlet in one of said passageways and an outlet in the other of said passageways, whereby sample flows through the intersection of said passageways.

7. The combination of claim 6, said sample cell body member being of generally rectilinear configuration, said fluid flow passageways comprising a pair of such passageways extending therethrough and intersecting each other at substantially a right angle, window means in at least one of the ends of at least one of said passageways for said energy in closely spaced relation to said intersection, whereby the energy from said source passes from said directing means through said window means to irradiate the sample at said intersection.

8. The combination of claim 6, said enclosure enclosing only said cell, said source means being mounted on a portion of said base member outside said enclosure, and said energy directing means being positioned in a wall of said enclosure between said source means and said cell.

9. The combination of claim 6, said enclosure enclosing said cell and said source means, and said energy directing means being positioned on said base member inside said enclosure between said source means and said cell.

10. The combination of claim 6, said energy directing means comprising beam collimator means and beam splitter means, and reference detector means mounted in a wall of said enclosure to receive a predetermined percentage of the energy from said source from said beam splitter means with the remainder of said energy passing through said beam splitter means to said cell.

11. The combination of claim 6, window means at an end of each passageway and light trap means at the opposite end of each passageway, heating means for said cell, and means to mount said heating means in contact with said cell.

12. The combination of claim 11, said cell body being of generally rectilinear configuration, said flow means comprising a flow inlet in one of said passageways and a flow outlet in the other of said passageways so positioned that sample will flow therebetween and through the intersection of said passageways, a plurality of mounting pads mounted on said base member to position said cell in predetermined spaced relation to said base member, said flow means further comprising an inlet and an outlet formed in respective ones of said pad members and cooperable with said cell flow inlet and outlet respectively, said heating means comprising a heater block configured to be positioned in said space between said cell and said base member when said cell is mounted on said pads and said flow means, and said heater block mounting means comprising a screw extending through said cell independently of said passageways therein and having its threaded end cooperating with a mating threaded opening in said heater block, whereby tightening off said screw at the head thereof on one side of said cell draws said heater block against the opposite side of said cell.

13. The combination of claim 12, and means to mount said cell with or without said heating means connected thereto in said enclosure comprising a screw extending through registering openings in said cell and said heater block when said heater block is mounted on said cell, and said screw comprising a threaded end fitting a threaded opening in said base member.

14. The combination of claim 12, and means to secure a lid on said enclosure and to locate said cell with or without said heating means connected thereto in said enclosure comprising a screw mounted in said lid and extending through registering openings in said block, independently of said passageways therein, and said heater block when mounted on said cell, and terminating at a mating threaded opening in said base member.

15. The combination of claim 11, means to mount an energy detection means in a wall of said enclosure in closely spaced relation to a window means in said cell, whereby the fluoresence re-emitted by the irradiated sample at the intersection of said passageways may be detected by means mounted on said energy detection mounting means.

16. The combination of claim 6, said cell being formed with a pair of intersecting passageways, said flow means comprising a pair of openings formed in said cell communicating with said passageways respectively, nozzle means mounted on said base member in positions thereon to communicate with said openings in said cell, and sealing means cooperative with said nozzle means and said openings respectively.

* * * * *